United States Patent
Rockley

(10) Patent No.: US 9,649,222 B2
(45) Date of Patent: May 16, 2017

(54) MULTI-PURPOSE PHACOEMULSIFICATION NEEDLE

(71) Applicant: Abbott Medical Optics Inc., Santa Ana, CA (US)

(72) Inventor: Paul W Rockley, Corona Del Mar, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 272 days.

(21) Appl. No.: 13/624,060

(22) Filed: Sep. 21, 2012

(65) Prior Publication Data

US 2013/0018383 A1    Jan. 17, 2013

Related U.S. Application Data

(62) Division of application No. 11/416,937, filed on May 2, 2006, now Pat. No. 8,287,484.

(51) Int. Cl.
*A61F 9/007* (2006.01)

(52) U.S. Cl.
CPC .............. *A61F 9/00745* (2013.01)

(58) Field of Classification Search
CPC ..... A61M 2205/058; A61M 2210/0612; A61F 9/0008; A61F 9/00736; A61F 9/00745; A61F 9/00754; A61F 9/00763; A61B 17/320068; A61B 17/320072; A61B 17/32008
USPC .......... 604/22, 264, 272; 606/107, 166, 167, 606/169
See application file for complete search history.

(56) References Cited

U.S. PATENT DOCUMENTS

| | | | |
|---|---|---|---|
| 3,732,858 | A | 5/1973 | Banko |
| 3,844,272 | A | 10/1974 | Banko |
| 4,047,532 | A | 9/1977 | Phillips et al. |
| 4,531,943 | A | 7/1985 | Van Tassel et al. |
| 4,689,040 | A | 8/1987 | Thompson |
| 4,808,153 | A | 2/1989 | Parisi |

(Continued)

FOREIGN PATENT DOCUMENTS

| | | | |
|---|---|---|---|
| EP | 0342448 | * | 11/1989 |
| EP | 1129681 A1 | | 9/2001 |

(Continued)

*Primary Examiner* — Imani Hayman
*Assistant Examiner* — Laura Schell
(74) *Attorney, Agent, or Firm* — Abbott Medical Optics Inc.

(57) ABSTRACT

In one aspect of the invention, a multi-purpose phacoemulsification needle comprises a needle body disposed about a centerline and has a lumen disposed therein. The lumen has a first cross-sectional area that is normal to the centerline. The needle further comprises a distal tip comprising an arcuate surface and a face with a port therein. The port has a second cross-sectional area in a plane generally parallel to the face and is in fluid communication with an internal cavity that has a third cross-sectional area normal to the centerline, the internal cavity being in fluid communication with the lumen. The needle is configured such that the third cross-sectional area is greater than either the first cross-sectional area or the second cross-sectional area. In another aspect of the invention, the needle comprises a plurality of fins projecting inwardly from the lumen.

10 Claims, 6 Drawing Sheets

(56) References Cited

U.S. PATENT DOCUMENTS

| | | | |
|---|---|---|---|
| 4,808,170 A | 2/1989 | Thornton et al. | |
| 4,816,018 A | 3/1989 | Parisi | |
| 4,869,715 A | 9/1989 | Sherburne | |
| 4,959,049 A | 9/1990 | Smirmaul | |
| 5,084,009 A | 1/1992 | MacKool | |
| 5,100,390 A | 3/1992 | Lubeck et al. | |
| 5,112,339 A | 5/1992 | Zelman | |
| 5,154,694 A | 10/1992 | Kelman | |
| 5,213,569 A * | 5/1993 | Davis | 604/22 |
| 5,242,385 A | 9/1993 | Strukel | |
| 5,254,106 A | 10/1993 | Feaster | |
| 5,286,256 A | 2/1994 | MacKool | |
| 5,290,267 A | 3/1994 | Zimmermann | |
| 5,295,980 A | 3/1994 | Ersek | |
| 5,451,229 A | 9/1995 | Geuder et al. | |
| 5,464,389 A | 11/1995 | Stahl | |
| 5,484,398 A | 1/1996 | Stoddard | |
| 5,515,871 A | 5/1996 | Bittner et al. | |
| 5,690,641 A | 11/1997 | Sorensen et al. | |
| 5,697,898 A | 12/1997 | Devine | |
| 5,725,495 A * | 3/1998 | Strukel | A61M 1/0035 604/22 |
| 5,733,266 A | 3/1998 | Gravlee, Jr. | |
| 5,743,871 A | 4/1998 | Strukel et al. | |
| 5,746,713 A | 5/1998 | Hood et al. | |
| 5,755,700 A | 5/1998 | Kritzinger et al. | |
| 5,788,679 A | 8/1998 | Gravlee, Jr. | |
| 5,836,926 A | 11/1998 | Peterson et al. | |
| 5,871,470 A | 2/1999 | McWha | |
| 5,980,529 A * | 11/1999 | Strukel | A61F 9/00745 604/19 |
| 5,989,209 A | 11/1999 | Barrett | |
| 5,993,408 A | 11/1999 | Zaleski | |
| 5,993,409 A | 11/1999 | Maaskamp | |
| 6,039,715 A | 3/2000 | MacKool | |
| 6,159,175 A | 12/2000 | Strukel et al. | |
| 6,299,591 B1 | 10/2001 | Banko | |
| 6,398,754 B1 | 6/2002 | Sutton et al. | |
| 6,398,759 B1 * | 6/2002 | Sussman et al. | 604/114 |
| 6,402,734 B1 | 6/2002 | Weiss | |
| 6,491,670 B1 | 12/2002 | Toth et al. | |
| 6,554,809 B2 | 4/2003 | Aves | |
| 7,588,553 B2 * | 9/2009 | Dewey | 604/22 |
| 2001/0031951 A1 * | 10/2001 | Pezzola | A61F 9/00745 604/275 |
| 2004/0193121 A1 | 9/2004 | Kadziauskas et al. | |
| 2004/0199192 A1 | 10/2004 | Akahoshi | |
| 2004/0267211 A1 * | 12/2004 | Akahoshi | 604/264 |
| 2006/0052758 A1 * | 3/2006 | Dewey | A61F 9/00745 604/272 |
| 2006/0217739 A1 * | 9/2006 | Tjia et al. | 606/107 |
| 2008/0058708 A1 | 3/2008 | Akahoshi | |

FOREIGN PATENT DOCUMENTS

| | | |
|---|---|---|
| EP | 1212995 A2 | 6/2002 |
| EP | 1464311 A1 | 10/2004 |
| WO | WO9422402 A1 | 10/1994 |
| WO | WO9638091 A1 | 12/1996 |
| WO | WO0174427 A1 | 10/2001 |

* cited by examiner

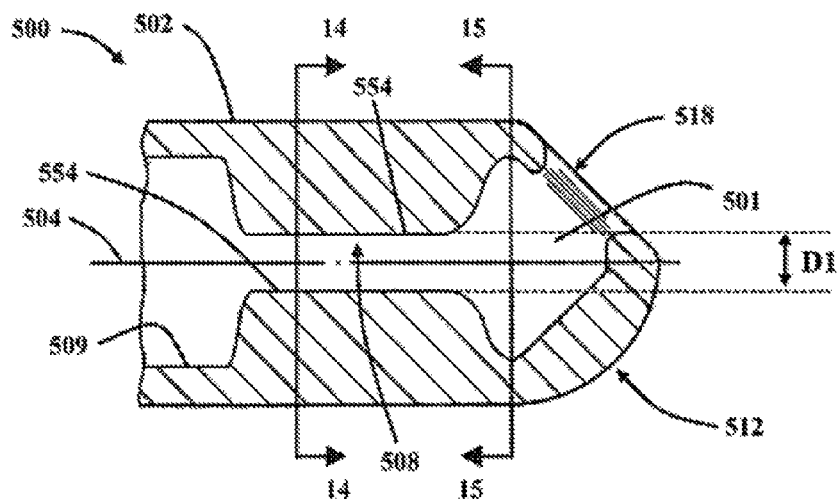
FIG. 13
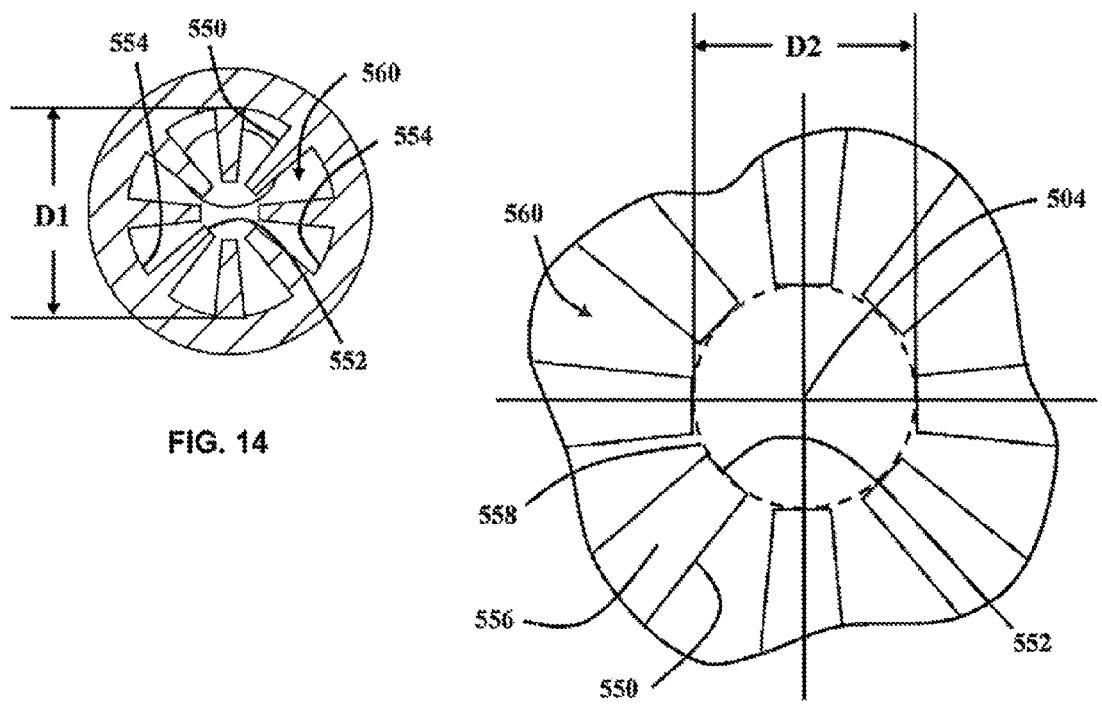
FIG. 14
FIG. 15

MULTI-PURPOSE PHACOEMULSIFICATION NEEDLE

This application is a divisional application of and claims priority to U.S. application Ser. No. 11/416,937 filed on May 2, 2006, which is hereby incorporated by reference in its entirety.

BACKGROUND OF THE INVENTION

Field of the Invention

The present invention generally relates to phacoemulsification needles and is more particularly directed to a multipurpose phacoemulsification needle.

Phacoemulsification refers to a method of lens and cataract extraction from an eye. The procedure includes an ultrasonically vibrated needle which is inserted through a very small incision of the cornea in order to provide energy for fragmenting the lens and cataract which then can be aspirated and removed through the incision.

The needle is supported by a handpiece interconnected with a console which provides electrical power to the handpiece as well as a supply of irrigation fluid and a vacuum source for aspiration of fragmented tissue and liquids.

The handpiece typically includes piezoelectric crystals or magnetostrictive elements which are coupled to the needle.

Often several needle types are utilized in the phacoemulsification procedure. For example, many needles utilize a relatively sharp surface in order to both enhance phacoemulsification and to break up the lens nucleus and cortex. However, any sharp edges can inadvertently cut the capsule surrounding the lens which may impair effective healing and prevent satisfactory visual recovery.

It is necessary, however, to remove soft cortical remnants of cataract tissue against the capsule and this often necessitates a second needle, or tool. This process effectively vacuums the internal surface of the lens capsule and is known as polishing.

The present invention provides for a multipurpose phacoemulsification needle suitable for both phacoemulsification of cataract and lens tissue as well as being affective for polishing the capsule.

SUMMARY OF THE INVENTION

A multipurpose phacoemulsification needle in accordance with the present invention generally includes a needle body having a lumen therethrough for aspiration of fluid and tissue. The needle body includes a proximal end adapted for attachment to a phacoemulsification handpiece and a distal end having a tip portion.

More specifically, the tip portion includes a truncated hemisphere having a flat surface thereon and a port disposed in the flat surface with the port communicating with the needle body lumen.

The tip can also be described as having a convex surface of revolution about a centerline of the tip portion which is defined by an arc extending from a circumference of the needle body to the tip portion centerline.

The surface of revolution provides for a rounded portion which includes sufficient area for polishing the eye lens capsule.

More particularly, the flat surface may extend from a centerline of the top portion to a tip portion circumference and include a bevel in the flat surface surrounding the port. This features insures that there will be no or minimal sharp edges in the needle distal end.

Still more particularly, the needle flat surface may be disposed at about a 45° angle with respect to the tip portion centerline.

The needle body may include a curved portion disposed adjacent the distal end tip portion which includes a curvature in a plane not including the flat surface.

Preferably, the plane is perpendicular to the flat surface and in one embodiment, the flat surface faces inward from an arc established by the needle body curved portion and in another embodiment, the flat surface faces outwardly from an arc established by the needle body curved portion.

The curved needle embodiments have additional advantage in the generation of cavitational energy, manipulating tissue within the eye during surgery and accessing cortex material from difficult to access locations within the eye during irrigation and aspiration.

In one aspect of the invention, a multi-purpose phacoemulsification needle comprises a needle body disposed about a centerline and has a lumen disposed therein. The lumen has a first cross-sectional area that is normal to the centerline. The needle further comprises a distal tip comprising an arcuate surface and a face with a port therein. The port has a second cross-sectional area in a plane generally parallel to the face and is in fluid communication with an internal cavity that has a third cross-sectional area normal to the centerline, the internal cavity being in fluid communication with the lumen. The needle is configured such that the third cross-sectional area is greater than either the first cross-sectional area or the second cross-sectional area.

In another aspect of the present invention, a multi-purpose phacoemulsification needle comprises a needle body having a lumen therethrough, the lumen having a primary surface with a first diameter. The lumen comprises at least three fins having isolated distal ends protruding inwardly from the lumen primary surface, the fins being configured such that a circle passing through the distal ends of the fins has a second diameter that is less than the first diameter. In addition, the fins each have a longitudinal extent along the centerline that is greater than the first diameter.

In yet another aspect of the present invention, a multi-purpose phacoemulsification needle comprises a needle body disposed about a centerline and having a lumen therethrough. The needle further comprises a distal tip comprising a flat surface with a port disposed therein. The flat surface is disposed at an acute angle relative to a portion of the centerline intersected by a line passing through the flat surface. The distal tip includes a continuous surface extending from a distal portion of the lumen to a distal portion of the needle body and free of discontinuities able to initiate a tear in a lens capsule of an eye when the capsule is invaginated by the phacoemulsification needle under normal ocular aspiration conditions.

In still another aspect of the present invention, a method of removing the natural lens of an eye comprises providing a multi-purpose phacoemulsification needle, according to an embodiment of the present invention. The method further comprises applying phacoemulsification power to the distal tip and removing at least a portion of the natural lens contained within the lens capsule of an eye. The method also comprises removing phacoemulsification power and passing the face of the distal tip of the needle over the surface of the lens capsule so as to remove cortical material therefrom. The method additionally comprises invaginating a portion of the lens capsule within the internal cavity and reapplying phacoemulsification power.

BRIEF DESCRIPTION OF THE DRAWINGS

The advantage of the present invention may be more readily understood by consideration of the following detailed description, particularly in conjunction with the accompanying drawings in which:

FIG. 13 is cross-sectional view of a phacoemulsification tip according to yet another embodiment of the present invention including a plurality of inwardly projecting fins disposed within a lumen.

FIG. 14 is a cross-sectional view of the phacoemulsification tip illustrated in FIG. 13 across a line 14-14.

FIG. 15 is a magnified, cross-sectional view of the phacoemulsification tip illustrated in FIG. 13 across a line 15-15.

DETAILED DESCRIPTION OF THE DRAWINGS

Figure 1:
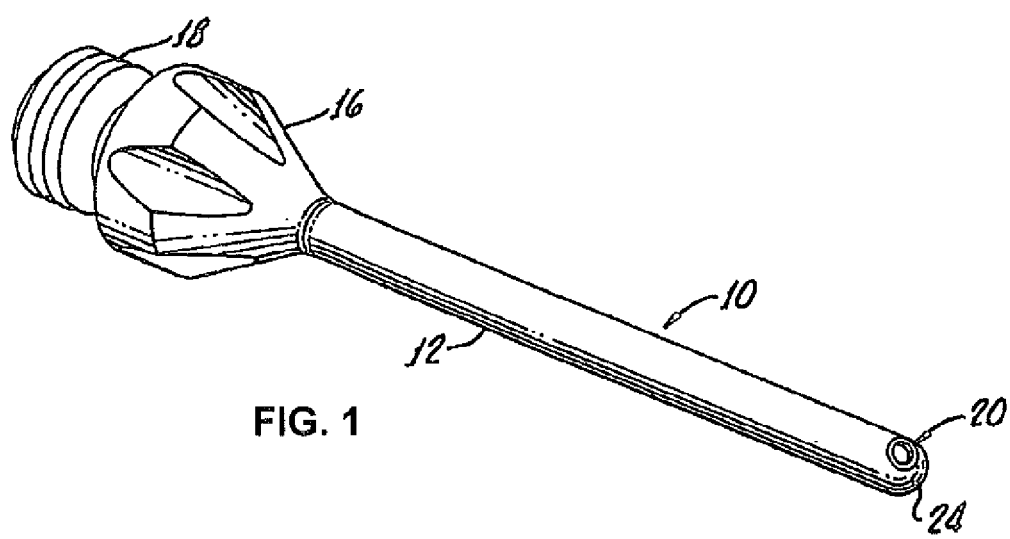
FIG. 1 is a perspective view of a multipurpose phacoemulsification needle in accordance with the present invention generally showing a needle body having a proximal and distal end with a tip portion disposed at the end.
Figure 2:
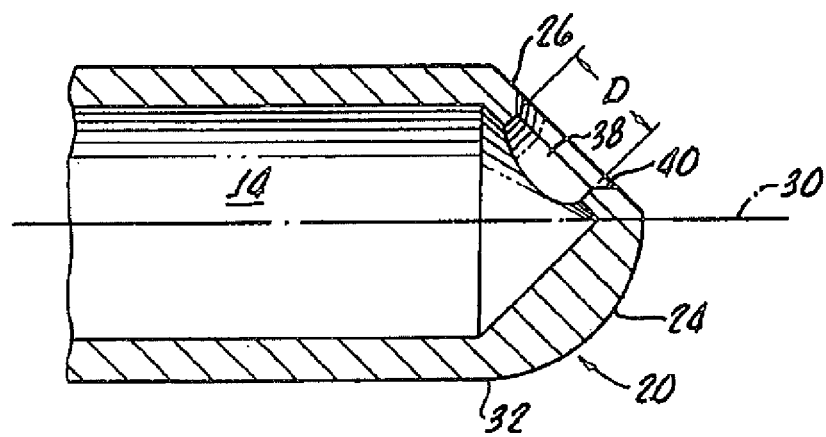
FIG. 2 is a cross-sectional view of the tip portion of the needle shown in FIG. 1.

With reference to FIG. 1, there is shown a multipurpose phacoemulsification needle 10 generally having a needle body 12 having a lumen 14 therethrough as shown in FIG. 2. The needle body includes a proximal end 16 which may include a threaded portion 18 which adapts the needle for attachment to a phacoemulsification handpiece, not shown. The needle 10 may be formed from a single piece of material suitable for phacoemulsification needle as is well known in the art.

A tip portion 20 of the needle body 12 includes a truncated hemisphere 24 having a flat surface 26 thereon. The flat surface 26 is preferably disposed from a location at or near the centerline 30 to a location at a distal end of the needle body 12.

The hemispherical surface 24 is formed by a convex surface of revaluation about a centerline 30 of the tip portion 20 defined by an arc extending from a circumference 32 of the needle 12 to the centerline 30.

The hemispherical or rounded surface 24 is of sufficient area for polishing an eye lens capsule as will be hereinafter described.

A port 38 is disposed in a flat surface 26 with the port 38 communicating with the needle body lumen 14 as most clearly shown in FIG. 2. A bevel 40 in the flat surface 26 surrounding the port, provides for a smooth entry through the port 38 and eliminates any sharp edges.

Preferably, the flat surface 26 is disposed at an angle of about 45 degrees (e.g., to within typical engineering tolerance, for example, 45 degrees±2 degrees or 45 degrees±1 degree) with a centerline 30. In some embodiments, the flat surface 26 is disposed at an angle of between about 25 degrees and about 65 degrees, preferably between 35 degrees and 55 degrees. In certain embodiments, the port diameter, D, is between 0.1 mm to about 0.5 mm, preferably between 0.15 mm and 0.45 mm, more preferably 0.2 mm to 0.4 mm or about 0.3 mm. In certain embodiments, the diameter, D, is chosen so as to restrict the aspiration flow rate of the needle 10 to be at or below a predetermined value, for example, so as to prevent the aspiration flow rate from exceeding a predetermined flow rate when an occlusion of the aspiration line breaks loose or is cleared.

Because of the rounded surface 24, and position of the port at a 45 degrees angle, the needle 10 is well suited for either cataract extraction and/or Irrigation and Aspiration (I/A) of the cortex. For example, the angled flat surface 26 may be disposed upon the needle 10 so that it may be conveniently directed toward the natural lens of an eye when phacoemulsification power is being used to remove portions of the natural lens. Later, when an I/A procedure is performed during the same surgical procedure, the rounded surface 24 of the same handpiece and needle 10 may be used to polish the lens capsule.

Figure 3:
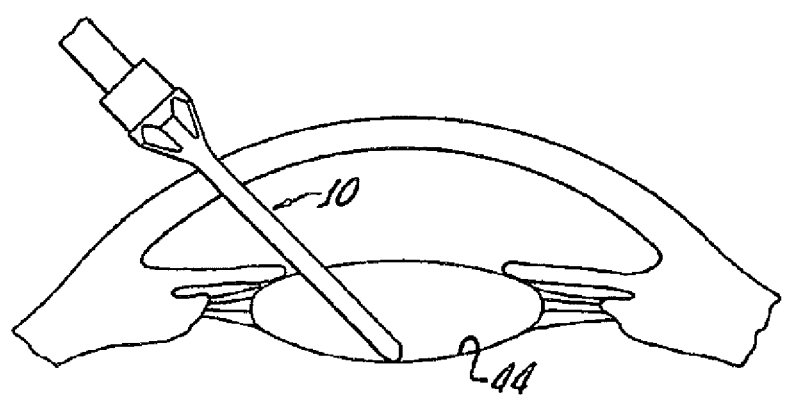
FIG. 3 is a representation of the needle function in polishing an eye capsule.

As illustrated in FIG. 3, the curved nature of the tip portion 20 and the significant area of the rounded portion 24, enables the surgeon to work close to a capsule and, in fact polish the capsule 44. Through the use of ultrasonic energy the needle may also be used (during I/A irrigation aspiration function) to remove cortex. Thus, a specific and important advantage of the present invention is that it eliminates the current need to use a separate handpiece to perform the I/A of a phacoemulsification procedure.

The present invention is easily distinguished over heretofore available phacoemulsification, such as for example, set forth in U.S. Pat. No. 5,980,529 which illustrates an off axis entry port but utilizes a angular or pointed end which is not amendable for lens capsule 44 polishing, and accordingly, is not a multipurpose needle.

Figure 4:
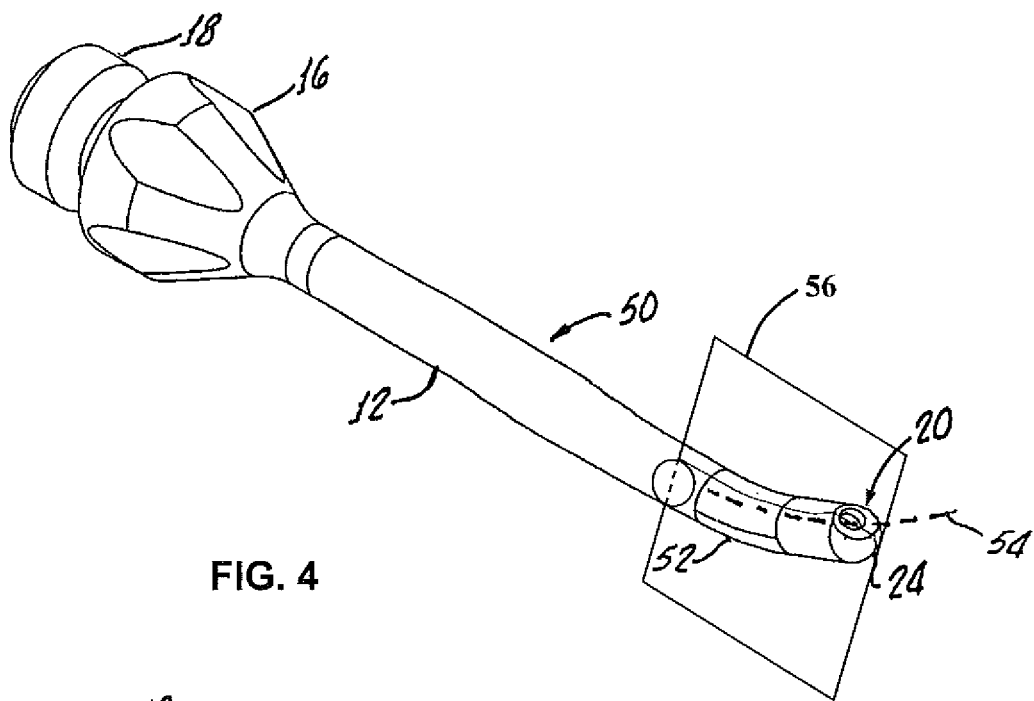
FIG. 4 is a perspective view of an alternative embodiment of the present invention similar to the embodiment shown in FIG. 1 but with a curved needle body portion.

With reference to FIG. 4, there is shown an alternative embodiment 50 in accordance with the present invention with common reference characters indicating substantially similar or identical elements of the invention as hereinabove described in connection with the embodiment shown in FIG. 1.

The multipurpose phacoemulsification needle 50 includes a curved portion 52 adjacent to the tip portion 20 having a curvature 54 in a plane 56 not including the flat surface 26, see FIG. 2. Preferably, the flat surface 26 is perpendicular to the plane 56 established by the curved portion curvature, or arc, 54.

In the embodiment 50, a flat surface 26 faces inwardly from the arc 54 established by the needle body curved portion 52.

Figure 5:
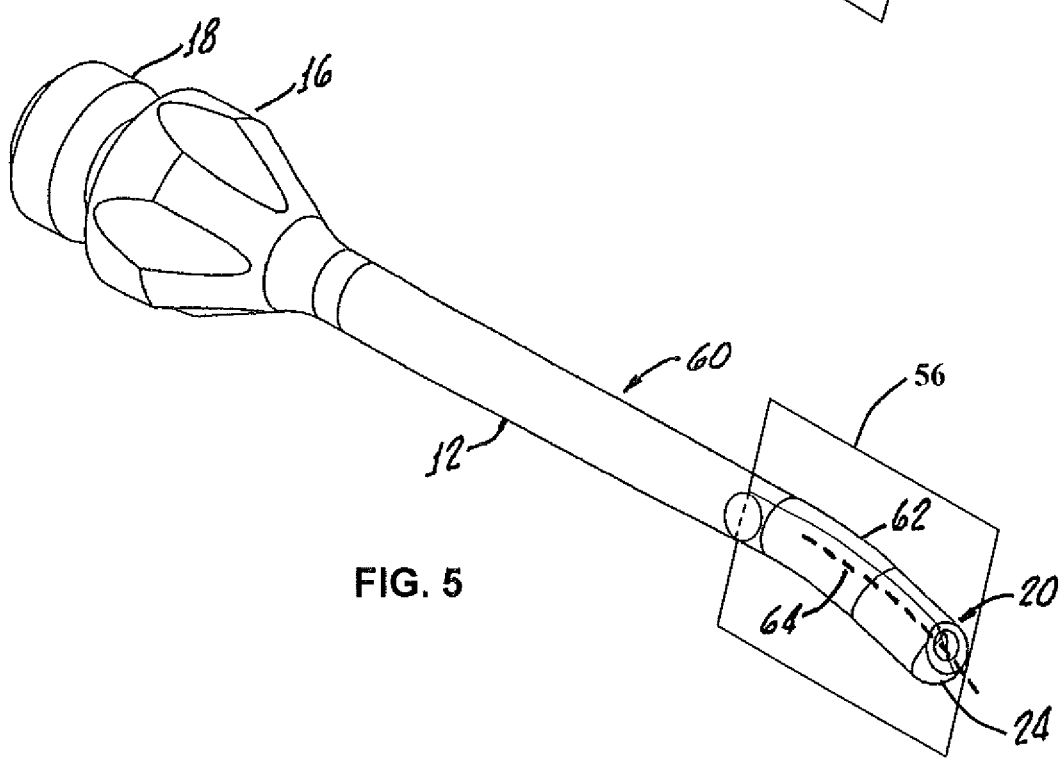
FIG. 5 is a perspective view of yet another embodiment of the present invention similar to the embodiment shown in FIG. 4 with a curved needle body portion, the curve being opposite that shown in FIG. 4.

With reference to FIG. 5, there is shown yet another embodiment 60 of a multipurpose phacoemulsification needle in accordance with the present invention with common reference numbers representing identical or substantially similar elements as hereinabove discussed in connection with FIGS. 1 and 4.

The phacoemulsification needle 60 is similar to the embodiment 50 shown in FIG. 4 except that a curved portion 62 is provided proximate the tip 20 which establishes an arc 64 opposite the arc 54 shown in FIG. 4 and in which the flat surface 64 faces outwardly from the arc 64 established by the needle body curved portion 62.

As hereinabove noted, these various phacoemulsification needle embodiments have the additional advantage in the generation of cavitational energy, manipulating tissue within the eye during surgery, as hereinabove noted, and accessing cortex material from difficult to access locations within the eye during irrigation and aspiration. The angle of curvature, or arc, 54, 64 may vary in the angle of the curvature or arc, the curvature depending upon the specific use intended for the needle 50, 60.

Figure 6:
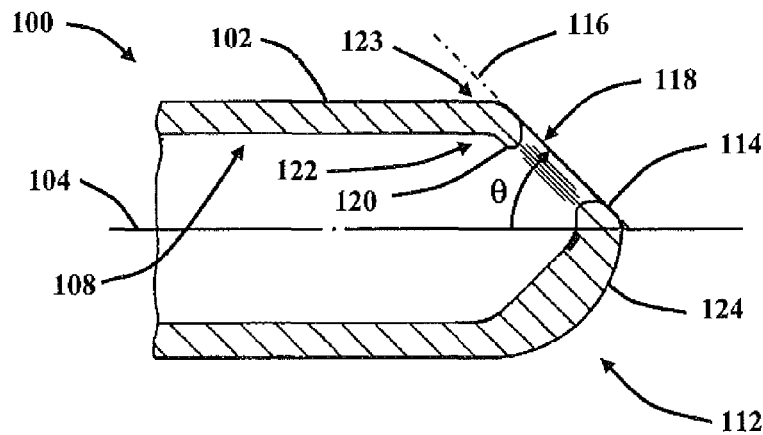
FIG. 6 is cross-sectional view of a phacoemulsification tip according to another embodiment of the present invention including a continuously smooth surface disposed about an opening at a distal end of the tip.

FIG. 6. illustrates a multi-purpose phacoemulsification needle 100 having a needle body 102. The needle body 102 may, for example, be straight, like the needle body illustrated in FIG. 1, curved like the needle body illustrated in FIG. 4, or some other shape suitable for an ocular surgical procedure. The needle body 102 is disposed about a centerline 104 and comprises a lumen 108 therein. The centerline 104 may be straight, as shown in FIG. 6, or may have at least a distal portion that is curved (e.g., like the arcs 54, 64 shown in FIGS. 4 and 5, respectively). The needle 100 further comprises a proximal end (not shown) and a distal tip 112. The proximal end is configured for attachment to a phacoemulsification handpiece. The distal tip 112 comprises a flat surface 114 disposed at an acute angle θ relative to a portion of the centerline 104 intersected by a line 116 passing through the flat surface 114. The distal tip 112 further comprises an opening or port 118 disposed within the flat surface 114 and communicating with the needle body lumen 108. The distal tip 112 includes a continuous surface 120 that is free of discontinuities and extending from a distal portion 122 of the lumen 108 to a distal portion 123 of the needle body 102. Preferably, the continuous surface 120 smoothly blends into a rounded surface 124 generally disposed and having sufficient area for polishing the lens capsule of an eye.

As used herein, the term discontinuity refers to a transition between two surfaces or surface portions that produce a visible corner or edge. While all physical corners and edges ultimately have a radius, a discontinuity, as it is used herein, pertains to a corner or edge that is visible as a discrete feature. As used in this context, "visible" refers to visible as seen by the naked eye, or with the assistance of certain low-power magnification devices, such as an ocular or a loupe. Another way of defining a discontinuity, as used herein, is as a portion or feature of surface at the distal tip of a phacoemulsification needle that has a sharp edge or a radius sufficiently small to initiate or propagate a tear in the wall of a lens capsule of a human eye when the capsule is invaginated by the needle under typical ocular surgical aspiration conditions.

The angle θ of the flat surface 114, combined with the inclusion of the rounded surface 124, allow the multi-purpose phacoemulsification needle 100 to be used advantageously in both phacoemulsification procedures and I/A procedures in which phacoemulsification power either is not supplied to the needle 100, or is supplied only for short periods of time, for example, on an as-needed bases to break apart lens material that causes the aspiration flow to become temporarily blocked or occluded. Preferably, the flat surface 114 is disposed at an angle of about 45° degrees (e.g., to within typical engineering tolerance). In some embodiments, the flat surface 26 is disposed at an angle of between about 25 degrees and 65 degrees, preferably between 35 degrees and 55 degrees. In other embodiments, the flat surface 114 is replaced by or combined with a concave or some other arcuate surface that is configured to help focus phacoemulsification power to a predetermined location in front of and/or above the needle 100. The single flat surface 114 may also be replaced by two or more surface portions that are either flat or arcuate and that are disposed at different angles relative to the centerline 104.

The continuous surface 120 enhances the versatility of the multi-purpose phacoemulsification needle 100 by, for example, allowing the surgeon to advantageously perform a variety of techniques with a single handpiece. For example, during some surgical procedures, instead of using the rounded surface 124, a surgeon may prefer to break apart or emulsify relatively soft and/or sticky cortical material remaining on the capsule surface by invaginating the capsule surface inside the needle 100. As with the needle 100, inner and outer surfaces of the distal tip 212 of phacoemulsification needle 200 are preferably configured to be smooth and free of any sharp edges or corners in order to protect the capsule surface from tearing during invagination.

Figure 7:
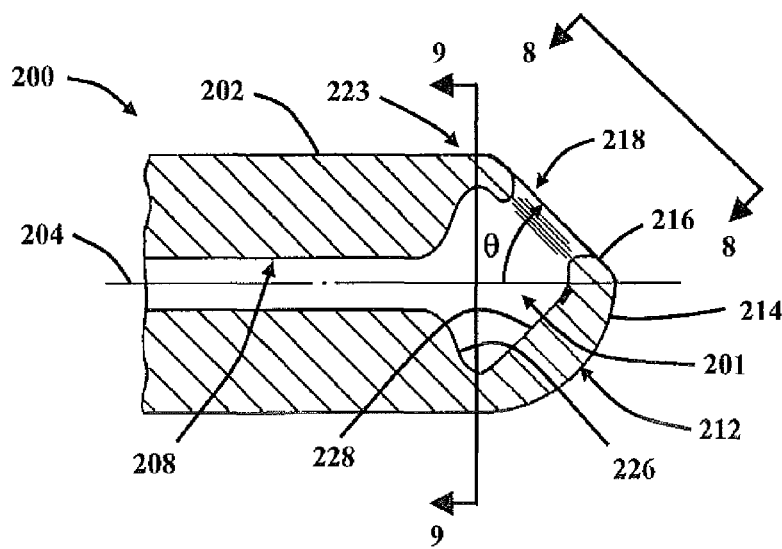
FIG. 7 is cross-sectional view of a phacoemulsification tip according to yet another embodiment of the present invention including an internal chamber at a distal end of the tip for receiving invaginated material.
Figure 8:
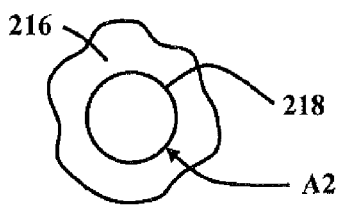
FIG. 8 is a front view of the phacoemulsification shown in FIG. 7.
Figure 9:
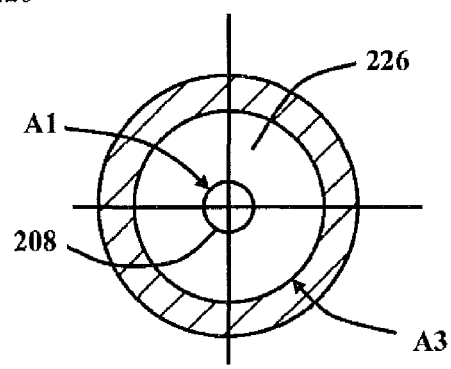
FIG. 9 is a cross-sectional view of the phacoemulsification tip illustrated in FIG. 7 across a line 9-9.

Referring to FIGS. 7-9, in certain embodiments, a multi-purpose phacoemulsification needle 200 is provided that is similar to the needle 100, with the additional feature that the needle 200 comprises an internal cavity 201 that is advantageously configured to enhance the ability of the needle to emulsify cataract and cortical lens material when a lens capsule is invaginated within the needle 200. The needle body 202 is disposed about a centerline 204 and includes a lumen 208 therein that has a cross-sectional area A1 in a direction normal to the centerline 204. The needle 200 further comprises a needle body 202 and a distal tip 212 comprising an arcuate surface 214 and a face 216 with an opening or port 218 therein.

Both the internal cavity 201 and the external portions of the distal tip 212 are configured to advantageously avoid tearing of the lens capsule during invagination thereof.

The port 218 has a cross-sectional area A2 in a plane generally parallel to the face 216 and is in fluid communication with the internal cavity 201. The internal cavity 201 has a cross-sectional area A3 normal to the centerline 204 and is in fluid communication with the lumen 208. Preferably, the cross-sectional area A3 of the internal cavity 201 is greater than both the cross-sectional area A1 of the lumen 208 and the cross-sectional area A2 of the port 218. In some embodiments, the cross-sectional area A2 of the port 218 may be equal to the cross-sectional area A3 of the internal cavity 201.

The generally larger dimension of the internal cavity 201 advantageously provides a cavity volume into which a section of the natural lens or an invaginated portion of the lens capsule may be drawn in by aspiration. In addition, the large dimension or size of the internal cavity 201 advantageously helps to provide a relatively large surface area for transmitting phacoemulsification power that may be used to emulsify cortical material still attached to the capsule wall. Because of the relatively large surface area, phacoemulsification power may be applied over a very short period of time to emulsify the cortical material, thus reducing the total amount of phacoemulsification energy necessary in performing this task.

As shown in the illustrated embodiment, the cross-sectional area A2 of the port 218 may be greater than the cross-sectional area A1 of the lumen 208. In such embodiments, the area A1 of the lumen 208 may be selected to restrict the aspiration flow rate to a predetermined value in order to protect the eye. The area A2 of the port 218 may, therefore, be sized independent of aspiration restriction requirements. For example the area A2 and/or the shape of the port 218 may be selected as a parameter in determining the size and/or shape of the portion of the lens capsule to be invaginated. Additionally or alternatively, the size and shape of the internal cavity 201 and/or the size and shape of the port 218 may be combined with periodic or occasional use of phacoemulsification power to the needle 200 to favorably break apart or emulsify pieces of the lens material that have a predetermined, characteristic dimension and/or shape.

The ports 118, 218 may be circular in shape, as illustrated in FIG. 8. In general, the ports 118, 218 may be sized and shaped according to specific design requirements. For example, the ports 118, 218 may be circular, as illustrated in FIG. 8, or elliptical or oval in shape. Alternatively, the ports 118, 218 may be in the form of a triangle, rectangle, or some other polygon shape, including star shaped. In some embodiments, the ports 118, 218 are in the form of a slit.

In certain embodiments, for example when needles 100, 200 are configured to be an aspiration flow restrictor, the ports 118, 218 have a diameter or effective diameter that between 0.1 mm to about 0.5 mm, preferably between 0.15 mm and 0.45 mm, more preferably 0.2 mm to 0.4 mm or about 0.3 mm. In other embodiments, the diameter or effective diameter of the ports 118, 218 is selected to be relatively large, for example, in a range of about 0.5 mm to about 0.7 mm, 0.7 mm to 1.0 mm, or greater than 1.0 mm.

In the illustrated embodiment, the distal tip 212 is straight and comprises a rounded bottom portion having a surface area configured for polishing an eye lens capsule. In other embodiments, the distal tip 212 curved and is disposed about a curved portion of the centerline 204.

The face 216 of the distal tip 212 is disposed from a location near the centerline 204 to a location at a distal end 223 of the needle body 202. The distal face 216 is preferably disposed at an angle relative to the centerline 204 in the vicinity thereof. In some embodiments, the distal face 216 is disposed at an angle of about 45° degrees (e.g., to within typical engineering tolerance). In other embodiments, the distal face 216 is disposed at an angle of between about 25 degrees and 65 degrees, preferably between 35 degrees and 55 degrees. The distal face 216 may be flat, as illustrated in FIG. 7 or may be concave (e.g., curved in at least one axis) or some other arcuate shape, for example, to help focus phacoemulsification power to a predetermined location in front of and/or above the needle 200.

The internal cavity 201 preferably comprises a proximal face 226, generally facing towards the port 218, and a distal face 228, generally facing toward the lumen 208. The faces 226, 228 are configured to direct phacoemulsification energy into the internal cavity 201, thus surrounding and concentrating phacoemulsification energy towards any cortical or other lens material contained inside the cavity 201. This configuration allows the needle 200 to emulsify lens material with a reduced amount of phacoemulsification energy. In some embodiments, the faces 226, 228 are substantially flat and angle so as to direct phacoemulsification energy toward the center of the cavity 201 and/or the centerline 204. Alternatively, at least portions of one or both of the faces 226, 228 are curved and may be disposed to focus energy to a location within the cavity 201. In certain embodiments, the faces 226, 228 are configured to focus or direct phacoemulsification energy to two or more locations so as to more effectively break or tear portions of entrapped lens material into portions of a predetermined characteristic dimension.

Figure 10:
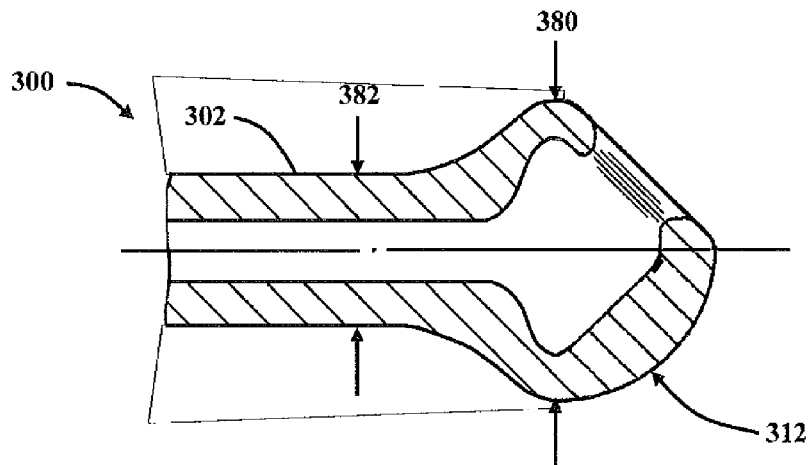
FIG. 10 is cross-sectional view of a phacoemulsification tip according to still another embodiment of the present invention including a needle body and a distal tip with an outer diameter that is greater than the outer diameter of the needle body.

Referring to FIG. 10, in certain embodiments, a multi-purpose phacoemulsification needle 300 comprises a needle body 302 and a distal tip 312. The needle 300 is substantially the same as the needle 200, except that the distal tip 312 has an outer diameter 380 that is greater than an outer diameter 382 of the needle body 302. The smaller diameter 382 may be selected, for example, to reduce the trauma to eye.

Figure 11:
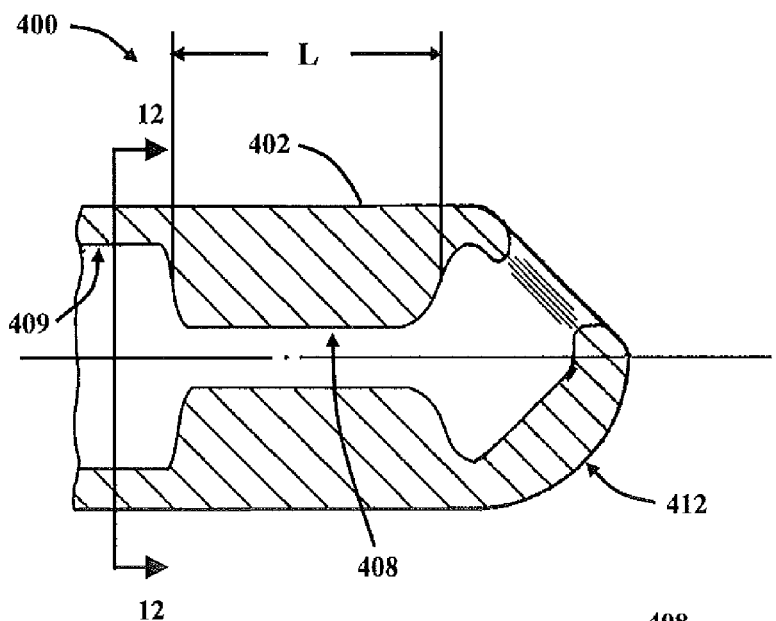
FIG. 11 is cross-sectional view of a phacoemulsification tip similar to the needle illustrated in FIG. 7 having a needle body lumen and a proximal lumen.
Figure 12:
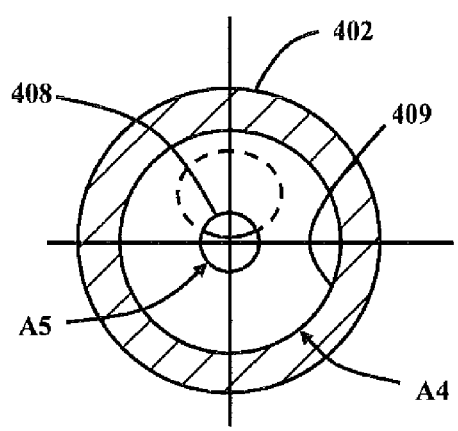
FIG. 12 is a cross-sectional view of the phacoemulsification tip illustrated in FIG. 11 across a line 12-12.

Referring to FIGS. 11 and 12, in certain embodiments, a multi-purpose phacoemulsification needle 400 comprises a needle body 402, a body lumen 408, and a distal tip 412. The needle 400 is substantially the same the needle 200, except that it comprises a proximal lumen 409 that is disposed proximal to and coaxial with the body lumen 408. The proximal lumen 409 has a cross-sectional area A4 that is greater than a cross-sectional area A5 of the body lumen 408. The cross-sectional areas A4, A5 shown in FIG. 12 are circular in form; however, either or both of the areas A4, A5 may be configured to have any convenient shape, including oval, square, rectangular, or starred. The smaller cross-sectional area A5 may be used as a flow restrictor, while the larger cross-sectional area A4 may be advantageously utilized to help prevent the needle 400 from becoming clogged by aspirated lens material. The needle body lumen 402 has a longitudinal length L, which preferably is greater than or equal to an outer diameter of the needle body 402.

Referring to FIGS. 13-15, a multi-purpose phacoemulsification needle 500 comprises a needle body 502 disposed about a centerline 504, a body lumen 508 disposed within the needle body 502, and a distal tip 512. The needle 500 is substantially the same the needle 400, except that the body lumen 508 comprises a plurality of fins 550 having isolated distal ends 552. The body lumen 508 comprises a primary surface 554 having a diameter D1. The fins 550 protrude inwardly from the surface 554 and preferably toward the centerline 504.

The fins 550 are preferably structured to help tear or emulsify lens material passing thereover. To aid in this process, the body lumen 508 may comprise at least three fins 550, preferably at least five fins 550 to as many as eight or more fins 550. Voids 560 between adjacent fins 550 provide an effective cross-sectional area of the body lumen 508 that is greater than the cross-sectional area of the circle 558. The voids 560 may thereby be used to provide greater aspiration flow rates through the needle 500, especially when the needle 500 becomes totally or partially occluded. In addition, the voids 560 may be used to increase or otherwise control the cross-sectional area of the lumen 508. The voids 560 may be in the shape of a circular sector.

The isolated distal ends 552 of the fins 550 in the illustrated embodiment shown in FIG. 15 are flat surfaces disposed about the centerline 504. In general, the isolated distal ends 552 may have any configuration or shape suitable for a particular set of design parameters. For example, the isolated distal ends 552 may be in the form of an arcuate surface and/or may be disposed at a different distances from the centerline 504. In addition, at least one of the distal ends 552 may have a shape or form that is different from that of the other distal ends 552. The isolated distal ends 552 are preferably configured such that a circle 558 passing through the ends 552 of the fins 550 has a diameter D2 that is less than the diameter D1 of the primary surface 554. In some embodiments, the isolated distal ends 552 are configured such that the diameter D2 of the circle 558 is less than 80 percent of the diameter D1 of the primary surface 554 of the body lumen 508, preferably less than 50 percent of the diameter D1, and in some cases less than 25 percent of the diameter D1.

The phacoemulsification needle 500 further comprises a port 518 similar to the ports 118 or 218. The port 518 may be configured to have a cross-sectional area that is less than the area of the circle 558 and/or less than the effective cross-sectional area of the body lumen 508, for example, when the port 518 is configured to be an aspiration flow restrictor. Alternatively, cross-sectional area of the port 518 may be selected to be greater than the effective cross-sectional area of the body lumen 508, for example, when the body lumen 508 is configured to be an aspiration flow restrictor.

The fins 550 are preferably structured to help tear or emulsify lens material passing thereover. To aid in this process, the body lumen 508 may comprise at least three fins 550, preferably at least five fins 550 to as many as eight or more fins 550. Voids 560 between adjacent fins 550 provide an effective cross-sectional area of the body lumen 508 that is greater than the cross-sectional area of the circle 558. The voids 560 may thereby be used to provide greater aspiration flow rates through the needle 500, especially when the needle 500 becomes totally or partially occluded. In addition, the voids 560 may be used to increase or otherwise control the cross-sectional area of the lumen 508.

The multi-purpose phacoemulsification needle 500 may further comprises a proximal lumen 509 that is disposed adjacent and proximal to the needle body lumen 408. In such embodiments, the fins 550 are preferably sufficiently rigid to prevent deformation thereof as aspirated fluid and other material passes over the fins 550. For example, the fins 550 may each have a longitudinal extent along the centerline 504 that is greater than the diameter D1 of the body lumen 508, preferably greater than a cross-sectional diameter of the lumen body 508.

Figure 16:
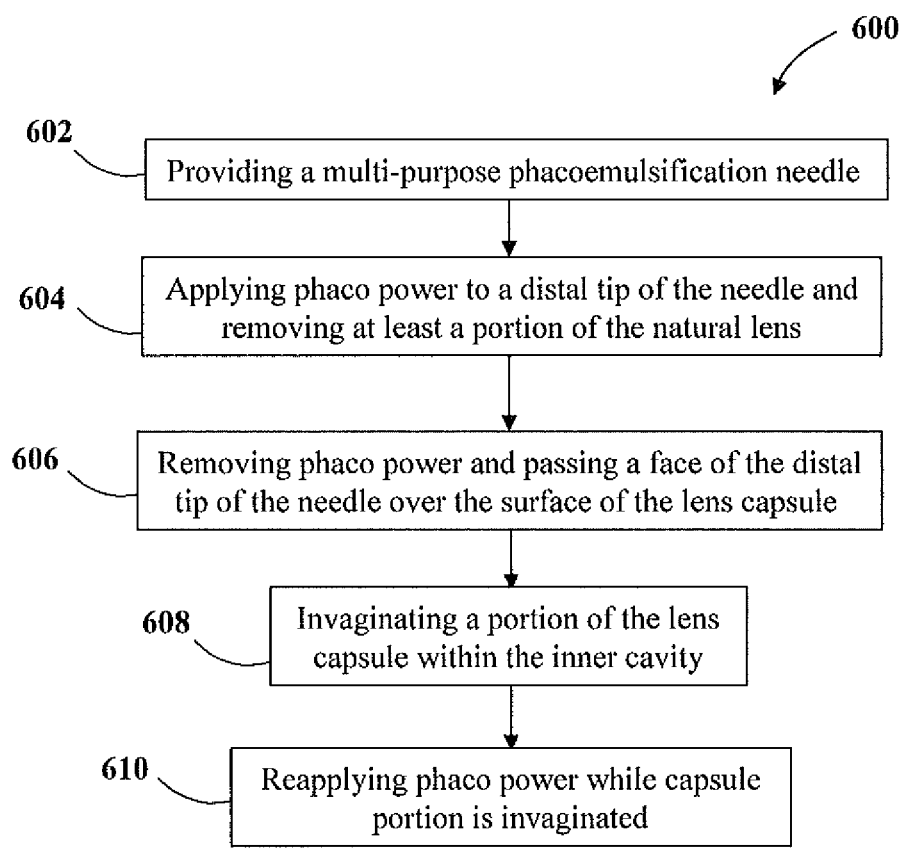
FIG. 16 is flow chart of a method of removing the natural lens of an eye.

Referring to FIG. 16, in certain embodiments, one of the multi-purpose phacoemulsification needles 100, 200, 300, 400, 500, or some variant thereof, are used in a method 600 of removing the natural lens of an eye. The method 600 comprises an operational block 602, providing a multi-purpose phacoemulsification needle according to an embodiment of the present invention. The method 600 further comprises an operational block 604, applying phacoemulsification power to a distal tip of the needle and removing at least a portion of the natural lens contained within the lens capsule of the eye. The method 600 also comprises an operational block 606, removing phacoemulsification power and passing a face of the distal tip of the needle over the surface of the lens capsule so as to remove cortical material therefrom. The method 600 additionally comprises an operational block 608, invaginating a portion of the lens capsule within the inner cavity. The method 600 also comprises an operational block 610, reapplying phacoemulsification power while capsule portion is invaginated.

Although there has been hereinabove described a specific curved multi-purpose phacoemulsification needle in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A multi-purpose phacoemulsification needle, comprising:
a needle body disposed about a centerline;
a lumen integral to the needle body along the centerline, wherein the lumen includes a primary surface and a first internal diameter; and
a proximal end adapted for attachment to a phacoemulsification handpiece; and
wherein the lumen includes at least three fins having isolated distal ends protruding inwardly from the primary surface of the lumen, the fins configured such that the distal ends of the fins create a second diameter that is less than 50% of the first internal diameter, wherein each of the at least three fins has a longitudinal extent along the centerline that is greater than the first internal diameter, and wherein the lumen comprises an internal cavity between the at least three fins and a distal end of the needle body.

2. The multi-purpose phacoemulsification needle of claim 1, wherein each of the isolated distal ends further comprises a distal face that is disposed at an angle to the centerline.

3. The multi-purpose phacoemulsification needle of claim 2, wherein each distal face of each of the fins is flat.

4. The multi-purpose phacoemulsification needle of claim 2, wherein each distal face of each of the fins is curved in at least one axis.

5. The multi-purpose phacoemulsification needle of claim 2, wherein the isolated distal ends are configured to focus phacoemulsification power toward a volume disposed about the centerline.

6. The multi-purpose phacoemulsification needle of claim 1, wherein the needle further comprises a distal tip, wherein the distal tip includes:
a rounded bottom portion having a surface area configured for polishing an eye lens capsule;
a top portion comprising a flat surface disposed from a location at or near the centerline to a location at the distal end of the needle body; and
a port disposed in the flat surface of the top portion, the port communicating with the lumen of the needle body.

7. The multi-purpose phacoemulsification needle of claim 6, wherein a cross-sectional area of the port is less than an area of a circle formed with the second diameter.

8. The multi-purpose phacoemulsification needle of claim 1, wherein the needle further comprises a distal tip comprising:
a flat surface disposed at an acute angle relative to the centerline;
a port disposed within the flat surface and communicating with the lumen of the needle body; and
a continuous outer surface free of discontinuities comprising the flat surface and a distal portion of the needle body.

9. The multi-purpose phacoemulsification needle of claim 1, wherein the fins are further configured to create voids between adjacent fins in a shape of a circular sector.

10. The multi-purpose phacoemulsification needle of claim 1, wherein the longitudinal extent is greater than an outer cross-sectional diameter of the lumen.

* * * * *